(12) United States Patent
Wolfaardt et al.

(10) Patent No.: US 12,241,887 B2
(45) Date of Patent: Mar. 4, 2025

(54) APPARATUS AND SYSTEM FOR MEASURING FOULING PARAMETERS IN A FLUID

(71) Applicant: STELLENBOSCH UNIVERSITY, Stellenbosch (ZA)

(72) Inventors: Gideon Wolfaardt, Stellenbosch (ZA); Kyle Brent Klopper, Stellenbosch (ZA)

(73) Assignee: STELLENBOSCH UNIVERSITY, Stellenbosch (ZA)

( * ) Notice: Subject to any disclaimer, the term of this patent is extended or adjusted under 35 U.S.C. 154(b) by 0 days.

(21) Appl. No.: 18/571,901

(22) PCT Filed: Jun. 23, 2022

(86) PCT No.: PCT/IB2022/055826
§ 371 (c)(1),
(2) Date: Dec. 19, 2023

(87) PCT Pub. No.: WO2022/269530
PCT Pub. Date: Dec. 29, 2022

(65) Prior Publication Data
US 2024/0264147 A1    Aug. 8, 2024

(30) Foreign Application Priority Data

Jun. 24, 2021   (ZA) ................................ 2021/04340

(51) Int. Cl.
*G01N 33/497*   (2006.01)
*G01N 21/59*    (2006.01)
(Continued)

(52) U.S. Cl.
CPC ......... *G01N 33/4977* (2024.05); *G01N 21/59* (2013.01); *G01N 21/85* (2013.01);
(Continued)

(58) Field of Classification Search
None
See application file for complete search history.

(56) References Cited

U.S. PATENT DOCUMENTS 2,743,167 A * 4/1956 Cherry ................... G01N 27/16
                                                       422/96
3,664,178 A * 5/1972 Spergel .............. A61B 5/02042
                                                       73/19.01
(Continued)

FOREIGN PATENT DOCUMENTS

JP           2005300375 A   * 10/2005

OTHER PUBLICATIONS

Translation of JP 2005300375A, Murotani,Norio, Oct. 27, 2005 (Year: 2005).*

(Continued)

*Primary Examiner* — Samuel P Siefke
*Assistant Examiner* — Henry H Nguyen
(74) *Attorney, Agent, or Firm* — Barnes & Thornburg LLP (57) ABSTRACT

An apparatus and system for measuring and monitoring fouling parameters in a fluid are provided. The apparatus includes a conduit within a housing, wherein at least a portion of the conduit provides a carbon dioxide permeable membrane through which carbon dioxide in the fluid can permeate in use. A carbon dioxide sensor within the housing is configured to measure carbon dioxide levels at the sensor. The housing further includes a light source that irradiates a portion of the conduit and a light sensor that is configured to measure light transmitted through or reflected by the irradiated portion of the conduit to measure the amount of fouling material within the fluid and attached to the irradiated portion of the conduit in use.

19 Claims, 8 Drawing Sheets

(51) Int. Cl.
    *G01N 21/85*    (2006.01)
    *G01N 21/94*    (2006.01)
(52) U.S. Cl.
    CPC ..... *G01N 21/94* (2013.01); *G01N 2021/8557* (2013.01); *G01N 2201/062* (2013.01)

(56) References Cited

U.S. PATENT DOCUMENTS

| | | | | |
|---|---|---|---|---|
| 5,247,826 A | * | 9/1993 | Frola | G01F 1/662 73/24.01 |
| 5,614,378 A | * | 3/1997 | Yang | C12M 21/02 435/293.1 |
| 5,714,758 A | * | 2/1998 | Neu | G01J 3/453 250/339.08 |
| 9,335,251 B2 | | 5/2016 | Syed et al. | |
| 2012/0258545 A1 | * | 10/2012 | Ash | A61M 1/1656 210/85 |
| 2014/0151538 A1 | * | 6/2014 | Syed | G01N 21/15 250/222.1 |
| 2015/0291993 A1 | * | 10/2015 | Vela | C12Q 1/06 210/745 |
| 2015/0323468 A1 | * | 11/2015 | Nakano | G01L 11/02 422/86 |
| 2019/0353593 A1 | * | 11/2019 | Ryu | G01N 21/59 |

OTHER PUBLICATIONS

Kroukamp et al. "CO2 Production as an Indicator of Biofilm Metabolism," Applied And Environmental Microbiology, American Society for Microbiology, vol. 75(13): 4391-4397 (Apr. 3, 2009).

Vanrolleghem et al., "On-line monitoring equipment for wastewater treatment processes: state of the art,"Water Science & Technology, vol. 47(2): 1-34 (Jan. 1, 2003).

Search Report & Written Opinion issued in Appl. No. PCT/IB2022/055826 (Sep. 27, 2022).

* cited by examiner

APPARATUS AND SYSTEM FOR MEASURING FOULING PARAMETERS IN A FLUID

CROSS-REFERENCE TO RELATED APPLICATIONS

This application claims priority from South African provisional patent application number 2021/04340 filed on 24 Jun. 2021, which is incorporated by reference herein.

This application is a U.S. nationalization under 35 U.S.C. § 371 of International Patent Application No. PCT/IB2022/055826 filed Jun. 23, 2022, which claims priority to ZA 2021/04340 filed Jun. 24, 2021; the entire contents of each are incorporated herein by reference.

FIELD OF THE INVENTION

This invention relates to an apparatus and system for measuring fouling parameters in a fluid. In particular, it relates to an apparatus and system for continuously monitoring microbial metabolic activity and the accumulation of biomass or other fouling material on surfaces in contact with the fluid.

BACKGROUND TO THE INVENTION

Fouling is the accumulation of unwanted material on solid surfaces of a component, system, or plant performing a defined function. Fouling may eventually interfere with the functioning of the component, system, or plant. Fouling materials can consist of either living organisms (biofouling) or non-living substances (inorganic or organic). Biofouling or biological fouling is the undesirable accumulation of micro-organisms, algae and diatoms, plants, and animals on surfaces, for example, on surfaces of piping and reservoirs with untreated water. Biofouling may cause microbiologically influenced corrosion (MIC).

Microbes such as bacteria can form biofilms on solid surfaces. Biofilm formation may be detrimental to human health, particularly in cases of biofilm-associated contamination of food, pharmaceuticals, or other products. It is therefore crucial that production and other industrial plants that make use of fluid transport and/or storage systems, particularly those involving water or aqueous solutions, keep track of biofilm development and devise suitable treatment strategies.

Biofilms have complex structures and are dynamic. Owing to their complexity, the term "biofilm biomass" may be interpreted to include cellular and noncellular fractions of biotic origin, as well as inorganic matter. Biofilms change readily in response to environmental conditions. The methods commonly used to analyse biofilms are labour intensive and involve periodic measurements. They are often destructive and provide only end-point analyses. For example, biofilm biomass can be accurately quantified in terms of total protein content, but this requires destructive sampling which renders it unsuitable for continuous monitoring of biofilm development. Further specialised techniques such as confocal laser scanning microscopy and attenuated total reflectance Fourier-transform infrared spectroscopy may be used to analyse biofilm biomass. However, these techniques are often complex and involve large, intricate, and expensive equipment.

Accordingly, there is a need for an apparatus and system that is capable of measuring fouling parameters in a fluid continuously to establish a level of biofouling within a particular fluid source, fluid system or process. The information obtained in this manner is useful for informing system operators in real-time of any maintenance that may be required.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with an aspect of the invention there is provided an apparatus for measuring fouling parameters in a fluid comprising:
  a housing;
  a conduit within the housing, wherein at least a portion of the conduit provides a carbon dioxide permeable membrane;
  a carbon dioxide sensor within the housing configured to measure carbon dioxide levels at the sensor;
  a light source within the housing that irradiates a portion of the conduit; and
  a light sensor within the housing configured to measure light transmitted through or reflected by the irradiated portion of the conduit.

The conduit may be a tube that is at least partially wound or looped within the housing. The housing may be generally cylindrical and the tube partially wound into a coil. The tube may be coiled around a central shaft mounted centrally within the cylindrical housing. The central shaft may include a plurality of guides for the coiled tube that are arranged to space helical rings of the coiled tube apart.

The conduit may be formed from a carbon dioxide permeable silicone membrane. The conduit may be about 2 meters long.

The conduit may carry the fluid through the housing and have one end at a fluid inlet port of the housing and an opposite end at a fluid outlet port of the housing. Changes in the carbon dioxide levels as measured by the carbon dioxide sensor may indicate a relative amount of carbon dioxide diffusing through the carbon dioxide permeable membrane. The housing may include a lid that is secured to a body of the housing. The lid may include the fluid inlet port and the fluid outlet port of the housing. The apparatus may include a pump configured to circulate the fluid between the fluid inlet port and the fluid outlet port. The pump may be configured to circulate the fluid continuously. The housing may further include an air inlet port and an air outlet port, the air outlet port including an elongate pipe that extends into the housing with its open end near the carbon dioxide sensor. The air outlet port may be connected to a pump for continuous removal of air from the housing. The air inlet port and air outlet port may be provided in the lid. The lid may also include a connector for electric wiring of the sensors that extend through the central shaft.

Alternatively, the housing may include a plurality of openings for the fluid so that, in use, the conduit is immersed in the fluid with the conduit carrying a carrier gas and having one end at an gas inlet port of the housing and an opposite end at a gas port into a carbon dioxide measurement chamber. The carbon dioxide sensor may then be configured to measure the carbon dioxide levels in the carbon dioxide measurement chamber. In this embodiment, the carbon dioxide measurement chamber may include a gas vent through which the carrier gas may exit in use. The apparatus may include a pump configured to circulate carrier gas between the gas inlet port and the gas vent. The gas inlet port may be connected to a pump for continuous pumping of carrier gas though the conduit and into the carbon dioxide measurement chamber. The carbon dioxide measurement chamber may also include a connector for electric wiring of the sensors that extend through the central shaft and carbon dioxide measurement chamber. The carrier gas may be air.

The carbon dioxide sensor may be mounted on a generally vertical support to, in use, ensure adequate gas flow around the sensor.

The conduit may include a generally straight portion that extends through an optical chamber which houses the light source and the light sensor on opposite sides of the generally straight portion of the conduit. The light source may be a light emitting diode (LED) and the light sensor may be a digital light sensor that measures light transmission through the conduit. The optical chamber may also house a light filter arranged to filter the light from the light source to light of a selected wavelength before measurement thereof by the light sensor. The optical chamber may connect to an end of the central shaft via a screw thread.

The apparatus may further include a processing module configured to receive a signal from the light sensor and process the signal to monitor the extent of biofouling and/or scaling of the conduit and to receive a signal from the carbon dioxide sensor and process the signal to monitor the levels of carbon dioxide produced by microbes in the fluid.

In accordance with a second aspect of the invention there is provided a system for monitoring fouling parameters in a fluid comprising the apparatus described above and a controller configured to be in communication with the light sensor and the carbon dioxide sensor of the apparatus to continuously monitor the fouling parameters measured.

The system may further include a warning component configured to be in communication with the controller and emit a warning signal if or when the fouling parameters measured by the apparatus and monitored by the controller reach a selected threshold level. The controller may then be configured to issue instructions to the warning component to emit varying types of warning signals based on the extent of fouling measured. The controller may be further configured to issue instructions to a dosing unit configured to dispense an antifouling agent into the fluid. The antifouling agent may be a biocide, bio-dispersant or a descaling agent.

Embodiments of the invention will now be described, by way of example only, with reference to the accompanying drawings.

DETAILED DESCRIPTION WITH REFERENCE TO THE DRAWINGS

An apparatus and system for measuring fouling parameters in a fluid are provided. The fluid may be any fluid or medium prone to fouling such as an industrial liquid or effluent that includes water or consists of mainly water. Fluids including water are prone to biofouling. The term "fouling parameters", as used herein, should be given its widest possible meaning by referring generally to the measurable factors present in a fluid that may result in fouling on solid surfaces in contact with the fluid and which can be detected with the sensors forming part of the apparatus and system described herein. One measurable factor may for example be the presence and accumulation of a living organism in the fluid, particularly microbes, which may be detected with optical measurements and/or the measurement of carbon dioxide respiration or production rates. Another fouling parameter or factor may be the presence of inorganic material or minerals in the fluid which causes scaling on solid surfaces which is also detectable by optical measurements.

The apparatus for measuring fouling parameters in a fluid includes a conduit within a housing, wherein at least a portion of the conduit provides a carbon dioxide permeable membrane through which carbon dioxide in the fluid can permeate in use. A carbon dioxide sensor within the housing is configured to measure carbon dioxide levels at the carbon dioxide sensor, in particular changes in carbon dioxide levels. The changes in the carbon dioxide levels as measured by the carbon dioxide sensor indicate a relative amount of carbon dioxide diffusing through the carbon dioxide permeable membrane. The carbon dioxide levels measured represent carbon dioxide production or respiration rates of living organisms, particularly microbes, which may be present in the fluid. The apparatus therefore provides means to monitor the metabolic activity of such organisms. The housing further includes a light source that irradiates a portion of the conduit and a light sensor that is configured to measure light transmitted through or reflected by the irradiated portion of the conduit. The optical measurements with the light sensor are useful for monitoring the amount of fouling material, particularly solids, within the fluid and attached to the irradiated portion of the conduit in use. The fouling material may be attached or detached or free-flowing biomass and may also include other solid deposits such as minerals on the surface of the conduit.

Figure 1:
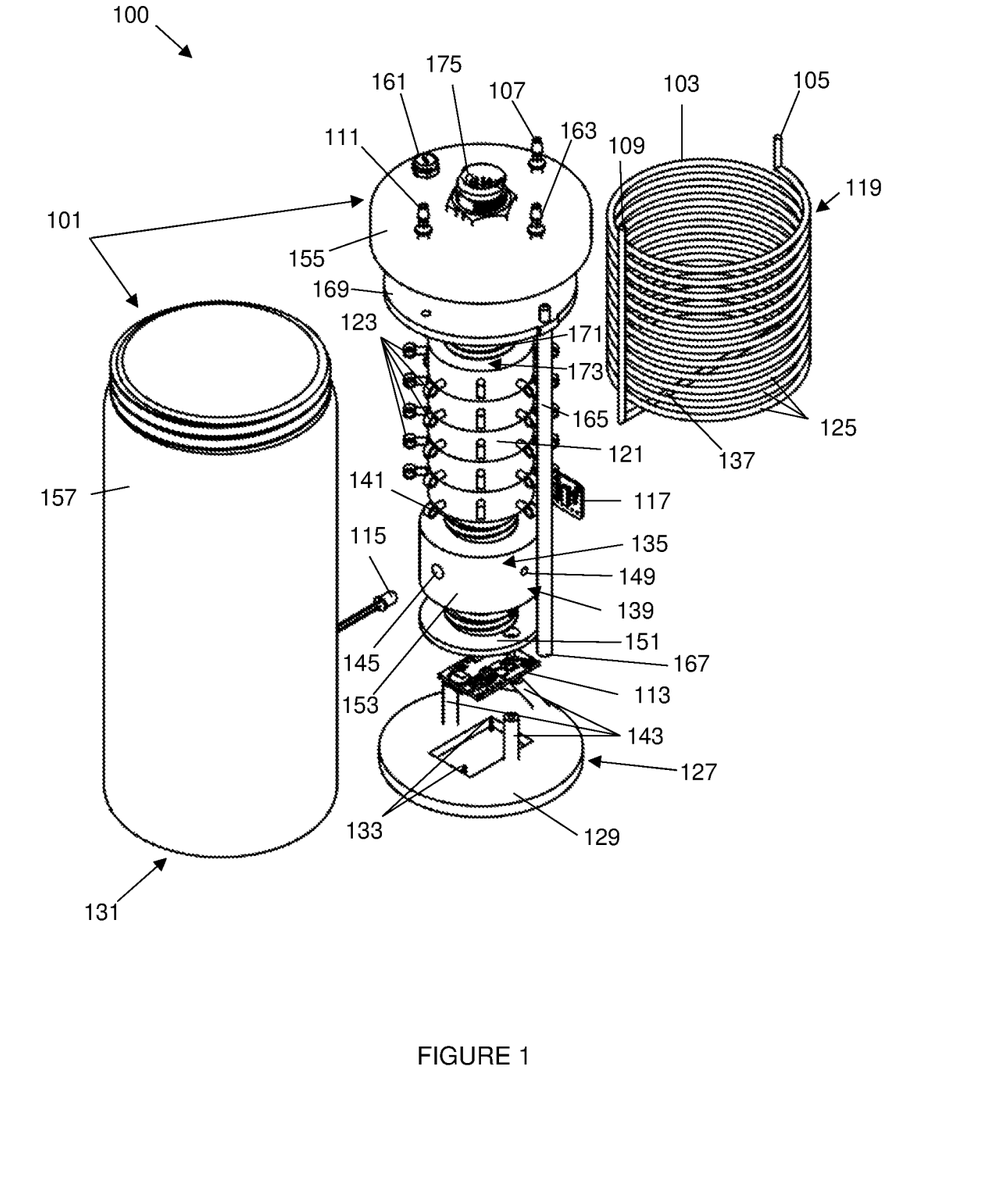
FIG. 1 is a top perspective view of a first embodiment of an apparatus for measuring fouling parameters in a fluid in a disassembled condition.
Figure 2:
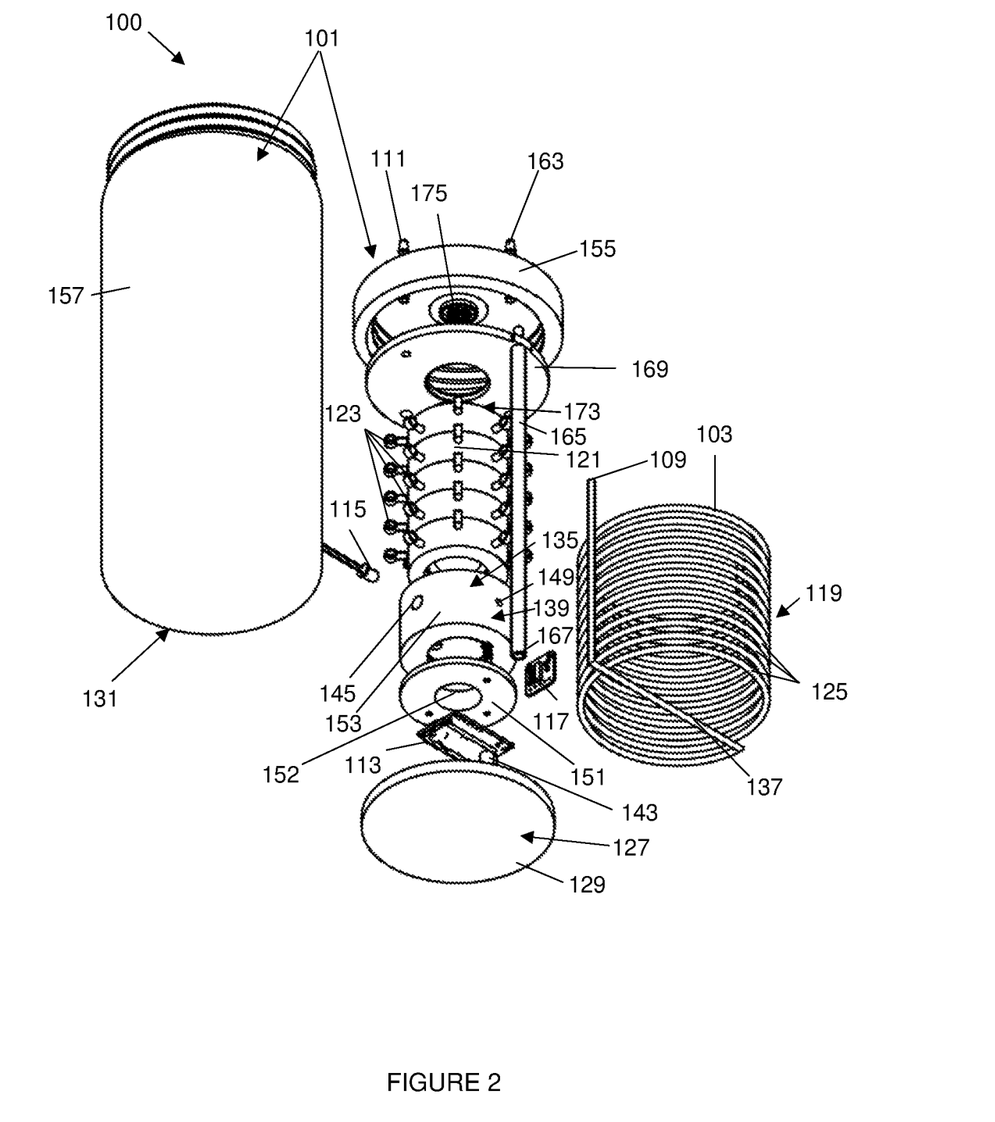
FIG. 2 is a bottom perspective view of the embodiment of FIG. 1 in a disassembled condition.
Figure 3:
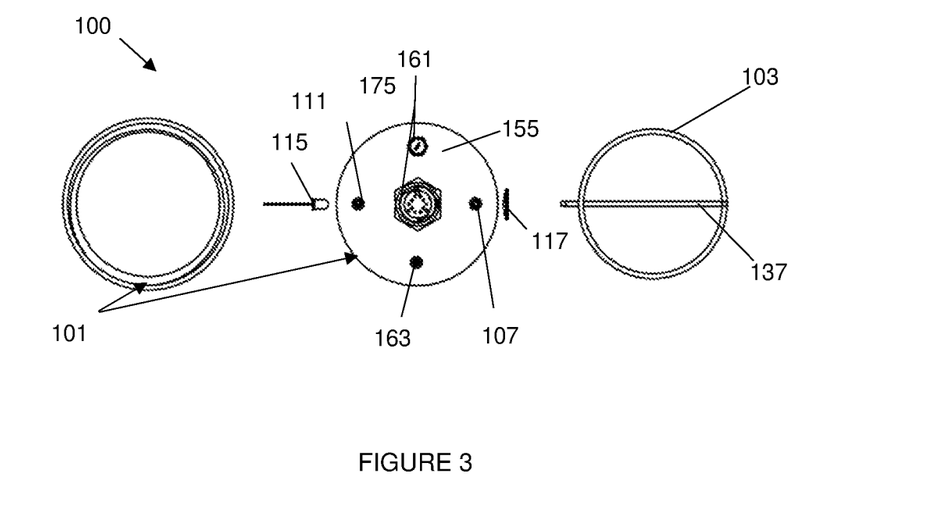
FIG. 3 is a top view of the embodiment of FIG. 1 in a disassembled condition.
Figure 4:
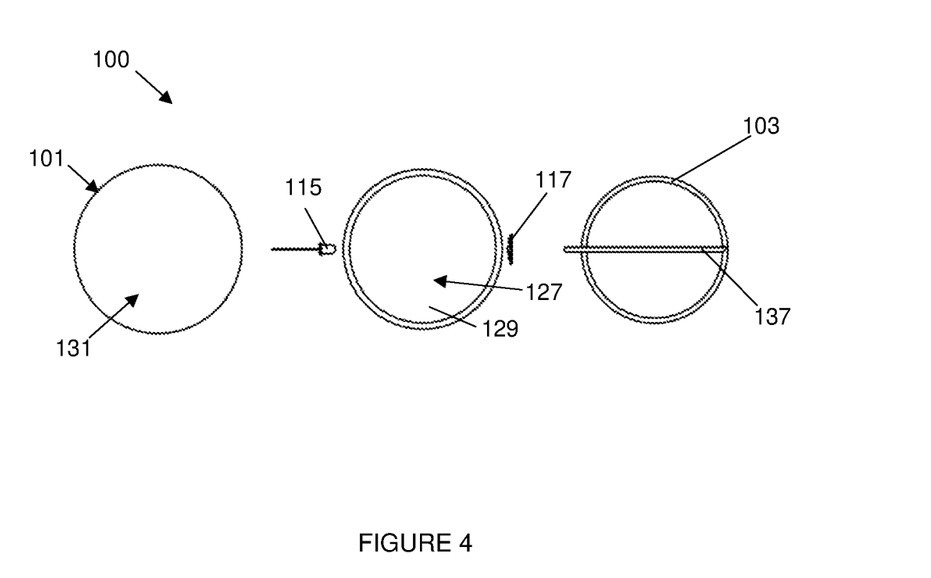
FIG. 4 is a bottom view of the embodiment of FIG. 1 in a disassembled condition.
Figure 5:
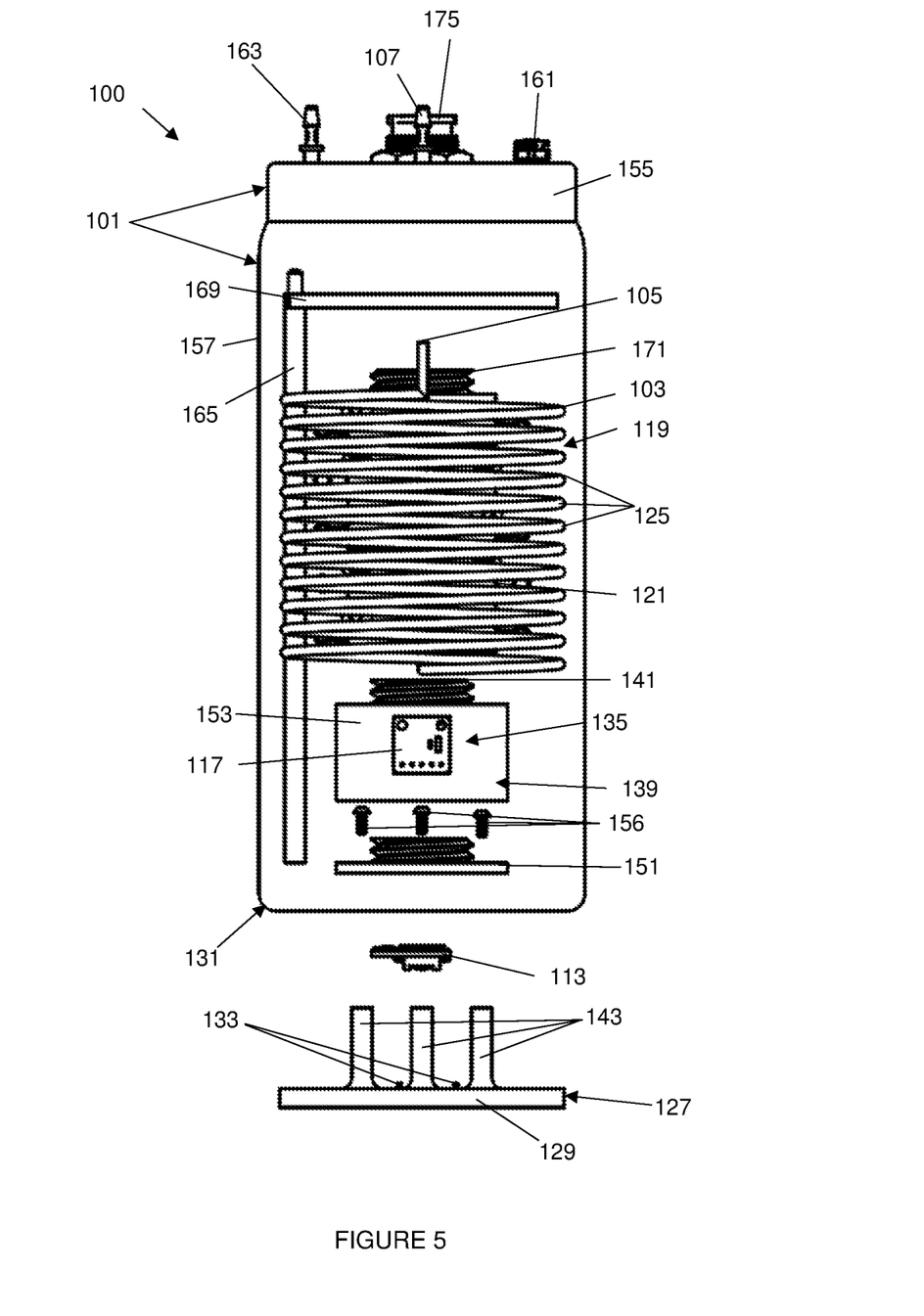
FIG. 5 is a front view of the embodiment of FIG. 1 in a partly assembled condition.

A first embodiment of an apparatus (100) for measuring fouling parameters in a fluid is shown in FIGS. 1 to 5 and includes a housing (101) that encloses a conduit (103). As is shown most clearly in FIGS. 2 and 5, the conduit has one end (105) at a fluid inlet port (107) of the housing (101) and an opposite end (109) at a fluid outlet port (111) of the housing (101). The conduit (103) carries the fluid through the housing (101) and is at least partially permeable to carbon dioxide. At least a portion of the conduit, but preferably the whole conduit, comprises a carbon dioxide permeable membrane so that carbon dioxide respired by microbes or other living organisms that may be present in the fluid can permeate through the membrane and into the housing (101) where changes in carbon dioxide levels are measured in the housing by a carbon dioxide sensor (113) located within the housing (101) as shown in FIGS. 1, 2 and 5.

The housing further encloses a light source (115) arranged to irradiate a portion of the conduit (103) and a light sensor (117) that is configured to measure light transmitted through or reflected by the irradiated portion of the conduit (103). The light transmission or reflectance measurements obtained in this manner are useful for monitoring for the potential accumulation of attached or free-floating material in the conduit. For example, microbial surface adhesion (biofouling) or scaling on the inner surface of the conduit can be detected by sensing changes in light transmission or reflectance along the irradiated portion of the conduit. The apparatus (100) is therefore configured to measure at least two fouling parameters in a fluid simultaneously by transporting fluid through a single conduit (103) enclosed in a housing (101) that also houses the carbon dioxide sensor (113) and light sensor (117). In other words, the same fluid from a surrounding fluid environment passes through the conduit (103) providing one line for measuring microbial metabolism and light transmission/reflectance. The apparatus (100) is capable of monitoring microbial metabolism in real-time by measuring changes in the levels of carbon dioxide respired by the microbes and changes in the amount of fouling material in the fluid in situ and under continuous flow of the fluid through the conduit (103).

In the embodiment shown in FIGS. 1 to 5, the conduit (103) is a tube formed from a carbon dioxide permeable silicone membrane. As is shown most clearly in FIG. 5, the conduit (103) is wound into a helix or coil (119) around a central shaft (121) which is shown in FIGS. 1 and 2, to increase the length of tube enclosed in the housing and thus also the surface area available for carbon dioxide permeation into the housing (101). In this embodiment, the conduit is about 2 meters long. The central shaft (121) may be in the form of a hollow column mounted centrally within the cylindrical housing (101). The central shaft (121) includes a plurality of guides (123) for the coiled tube or conduit on its outer surface that are arranged to ensure spacing between the helical rings (125) of the coiled tube so that there is no contact between different portions of the tube, thereby ensuring that the maximum surface area of the tube is available for carbon dioxide permeation into the housing (101). The guides (123) are in the form of rings arranged in a helical arrangement on the outer wall of the central shaft (121). The conduit (103) passes through each of the rings and is supported in its coiled form by the helical ring arrangement.

In an assembled condition of the apparatus (100), the carbon dioxide sensor (113) is located operatively below the conduit (103). It is envisioned that this embodiment of the apparatus will be used with the housing (101) in a generally upright condition and, accordingly, any carbon dioxide produced by microbes or other living organisms in the fluid will collect within the operatively lower region of the generally upright housing (101). The carbon dioxide sensor (113) is mounted on a support (127) in the form of a mounting plate (129) shaped to be received in the operatively lower end (131) of the housing (101). The carbon dioxide sensor (113) is supported on two posts (133) extending from the mounting plate (129), which provides a vertical support, to ensure adequate air flow around the carbon dioxide sensor (113).

An optical chamber (135) is located in between the central shaft (121) and the carbon dioxide sensor (113) within the housing (101). The optical chamber comprises a cylindrical casing (139) connected or attached to the central shaft (121) via a screw thread (141). The casing (139) further includes a base plate (151), with a central aperture (152) for electrical wiring, that threadedly connects to the main cylindrical body (153) of the casing (139). The base plate (151) is secured to the mounting plate (129) with three fasteners (156) that fasten the base plate (151) to three spacers (143) extending from the mounting plate (129).

The main cylindrical body (153) of the casing (139) includes a first aperture (145) for receiving and supporting the light source (115) in the optical chamber and a second aperture on the opposite side of the cylindrical casing (139) for mounting the light sensor (117) opposite the light source. The conduit (103) is not entirely wound into a helix, but includes a generally straight portion (137) at the operatively lower end of the helix (119) that is configured to extend through the optical chamber (135) via two openings (149) on opposite sides of the main cylindrical body (153) of the casing (139). The optical chamber (135) is therefore configured to support the light source (115) and the light sensor (117) on opposite sides of the straight portion (137) of the conduit (103). This exemplary arrangement of the light source (115) and sensor (117) allows for light transmission through the conduit (103) to be measured. The light source (113) may be an LED that emits light of a selected wavelength and the light sensor (117) may be a digital luminosity sensor that measures light transmission through the conduit. The conduit must be made of a substantially transparent material to allow for the translucency of both the fluid and the conduit wall to be measured optically.

The housing (101) comprises a lid (155) that threadedly engages a cylindrical body (157) to be secured thereto. The lid (155) may include the fluid inlet port (107) and the fluid outlet port (111) of the housing (101). The apparatus may include a pump configured to circulate the fluid between the fluid inlet port (107) and the fluid outlet port (111). The pump may be configured to circulate the fluid intermittently or continuously, but preferably continuously to allow for continuous monitoring of fouling parameters in the fluid.

The lid (155) may further include an air inlet port (161) which may be a waterproof valve and an air outlet port (163), the air outlet port (163) including an elongate pipe (165) that extends into the housing (101) with its open end (167) in the operatively lower region of the housing (101) near the carbon dioxide sensor (113) to, in use, ensure removal of air, particularly the air that may contain higher concentrations of accumulated carbon dioxide, from the housing (101). The pipe (165) connects to the air outlet port (163) and extends from the air outlet port alongside the central shaft (121) and conduit (103) in the direction of the operatively lower end (131) of the housing (101). The pipe (165) is suspended from a circular disc (169) that fits over a screw thread (171) defined in the operatively upper end (173) of the central shaft (121) and is held captive between the lid (155) and the operatively upper end of the central shaft (121).

The air outlet port (163) may be connected to a pump for continuous removal of air from the housing (101). In this manner a carrier or sweeper gas, in this embodiment air, continuously flows though the housing to avoid carbon dioxide accumulation and ensure that carbon dioxide levels within the housing are continuously monitored. The lid (155) closes the housing (101) in an airtight or hermetic manner so that the only air that enters the housing (101) is that which enters through the air inlet port (161).

The lid (155) may further include a connector (175) for electric wiring of at least the sensors (113, 117), or the sensors (113, 117) and the light source (115), that may extend through the central shaft (121). The connector (175) may be a leakproof nylon connector that connects to the screw thread defined in the operatively upper end (173) of the central shaft (121). The connector (175) allows for the electronic signals of the sensors (113, 117) to be transferred to an external processing module. Accordingly, the apparatus (100) may further include a processing module configured to receive a signal from the light sensor (117) and process the signal to monitor the extent of biofouling and/or scaling of the conduit and to receive a signal from the carbon dioxide sensor (113) and process the signal to monitor the levels of carbon dioxide produced by microbes in the fluid.

Figure 6:
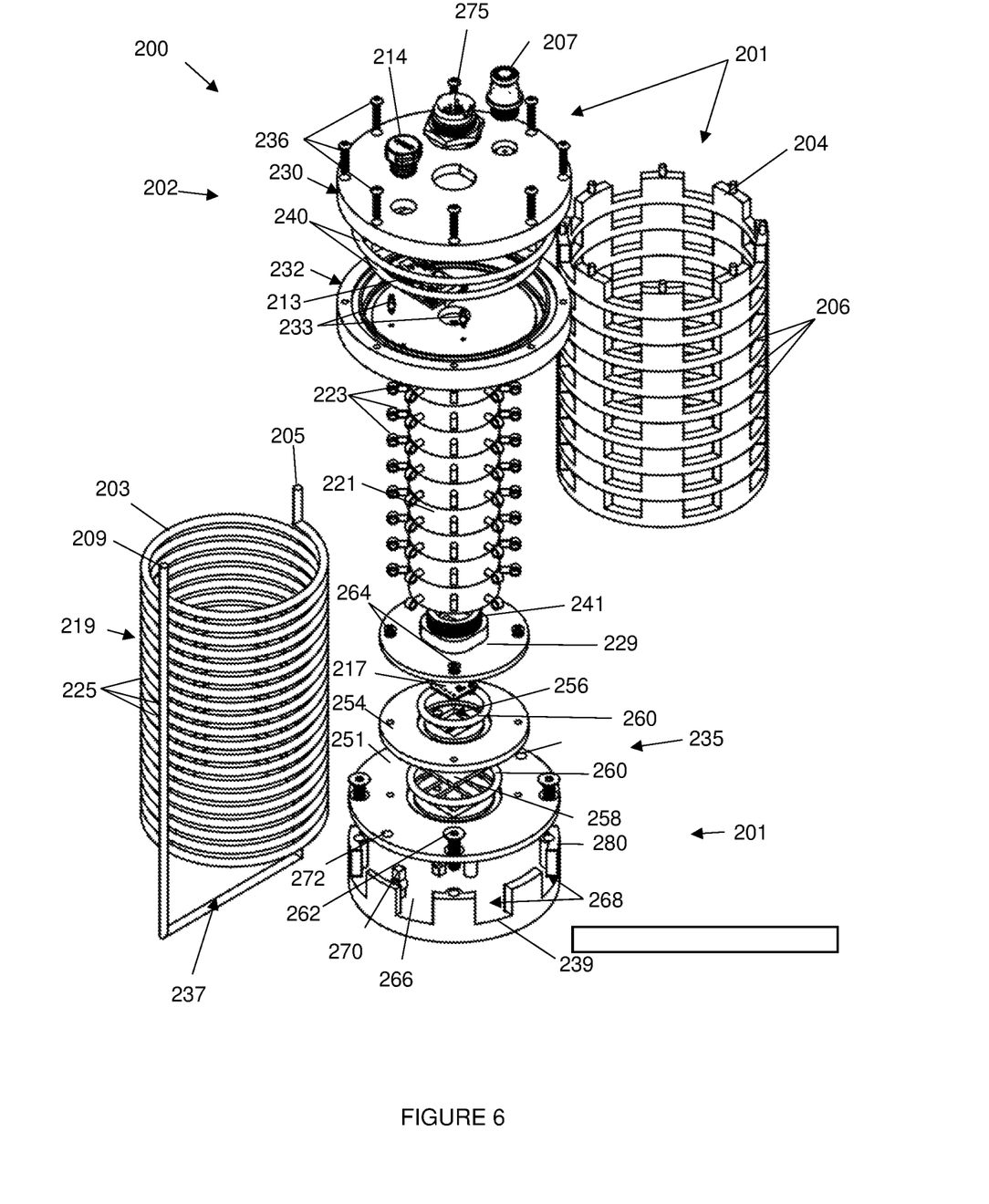
FIG. 6 is a top perspective view of a second embodiment of an apparatus for measuring fouling parameters in a fluid according to the invention in a disassembled condition.
Figure 7:
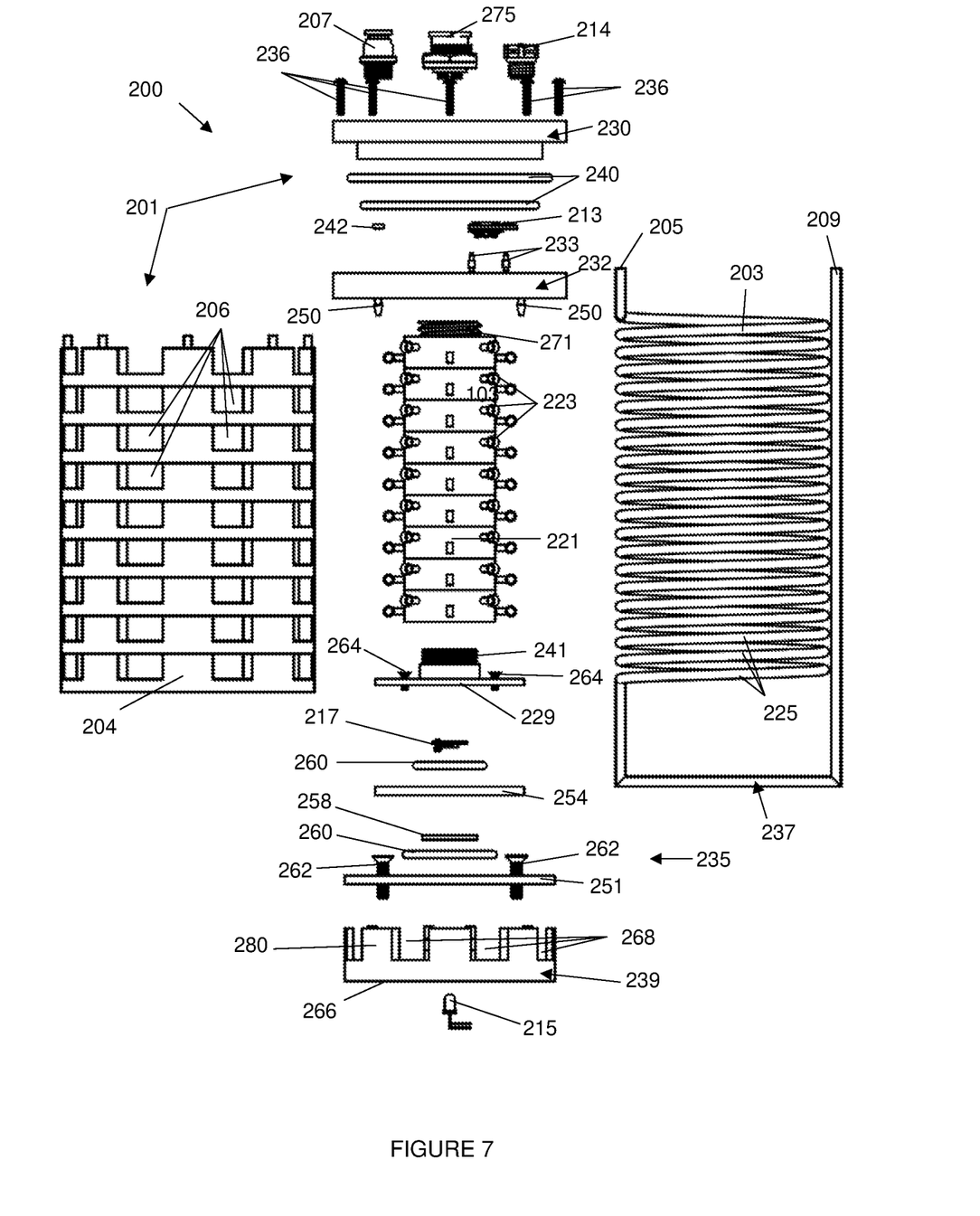
FIG. 7 is a side view of the embodiment of FIG. 6 in a disassembled condition.

A second embodiment of an apparatus (200) for measuring fouling parameters in a fluid is shown in FIGS. 6 and 7 and includes a housing (201) comprising a carbon dioxide measurement chamber (202), an optical chamber (235) and a protective cage (204) provided around a conduit (203). The housing (201), in particular the protective cage (204), includes a plurality of openings (206) for the fluid so that when the housing (201) is immersed in a fluid in use, the conduit (203) is also immersed in the fluid.

The conduit (203) is filled with a carrier gas and the conduit carries the gas though the housing (201). The conduit has one end (205) at a gas inlet port (207) of the housing (201) and an opposite end (209) at a gas port into the carbon dioxide measurement chamber (202). The gas port into the carbon dioxide chamber may include a barbed connector (250) for the conduit (203). The gas inlet port (207) allows transfer of either ambient air from the environment in the vicinity of the housing, or a carrier gas with a known, constant carbon dioxide concentration into the conduit (203). Depending on the layout of the fluid area to be monitored with the apparatus, a carbon dioxide impermeable tube may be required to transfer ambient air or carrier gas to the gas inlet port (207). In such case, the conduit (203) and carbon dioxide impermeable tube may be connected together via a suitable connector that may be a pneumatic or barbed connector, for example.

The conduit (203) is at least partially permeable to carbon dioxide. At least a portion of the conduit, but preferably the whole conduit, comprises a carbon dioxide permeable membrane so that carbon dioxide respired by microbes or other living organisms that may be present in the fluid can permeate through the carbon dioxide permeable membrane into the conduit (203) so that the carbon dioxide diffuses or is carried into the carbon dioxide measurement chamber (202) where changes in carbon dioxide levels are measured by a carbon dioxide sensor (213) located within the carbon dioxide measurement chamber (202).

The apparatus (200) may further include a pump configured to circulate the carrier gas between the gas inlet port (207) and a gas vent (214) in the carbon dioxide measurement chamber (202). The gas inlet port (207) may comprise a pneumatic connector with a rigid tube between the pneumatic connector and a barbed connector (250) on the carbon dioxide measurement chamber (202). The rigid tube extends through the carbon dioxide measurement chamber (202) and connects to the barbed connector (250), which receives the end (205) of the conduit (203), thereby connecting the conduit (203) to the pneumatic connector and pump for continuous pumping of carrier gas though the conduit (203) and into the carbon dioxide measurement chamber (202) where it exits through the waterproof gas vent (214). Carrier gas, whether atmospheric or prepared gas is therefore introduced into the conduit (203) via the pneumatic connector (207) linked to the barbed connector (250) via the larger and more rigid tube extending through the chamber (202). An O-ring (242) provides a gas-tight seal so that gas may be introduced into the end (205) of the conduit (203) without mixing/interacting with the gas entering the carbon dioxide measurement chamber (202) from the end (207) of the conduit (203) for the measurement of $CO_2$ concentration in the chamber (202). The analysed gas is then expelled out of the chamber (202) through the vent (214) as facilitated by the continuous introduction of "new" carrier gas into the conduit (203).

As is the case with the first embodiment, the conduit (203) is a tube formed from a carbon dioxide permeable silicone membrane and the conduit (203) is wound into a helix or coil (219) around a central shaft (221) to increase the length of tube enclosed in the housing and thus also the surface area available for carbon dioxide permeation into the conduit (203). Again, the conduit is about 2 meters long. The conduit may have an internal or inside diameter of between 2 mm and 3 mm, preferably about 2.5 mm. The central shaft (221) is in the form of a hollow column mounted centrally within the generally cylindrical housing (201). The central shaft (221) includes a plurality of guides (223) for the coiled tube or conduit (203) on its outer surface that are arranged to ensure spacing between helical rings (225) of the coiled tube so that there is no contact between different portions of the tube, thereby ensuring that the maximum surface area of the tube is available for carbon dioxide permeation into the conduit (203). The guides (223) are in the form of rings arranged in a helical arrangement on the outer wall of the central shaft (221). The conduit (203) passes through each of the rings and is supported in its coiled form by the rings.

The carbon dioxide measurement chamber (202) of the housing (201) which encloses the carbon dioxide sensor (213) comprises two parts (230, 232) secured together with a plurality of screws (236). The two parts (230, 232) are sealed in a manner to avoid ingress of fluid, in this embodiment with two nitrile O-rings (240). The first, operatively upper, part (230) or lid of the carbon dioxide measurement chamber (202) includes the gas inlet port (207) comprising the pneumatic connector, rigid tube and barbed connector connecting the conduit (203) to the pump. The first part (230) also includes the vent (214) and a cable connector (275) for electric wiring of the sensors (213, 217) that extend through the central shaft (221) and carbon dioxide measurement chamber (202). The cable connector (275) is an industrial weather-proof cable connector. The second, operatively lower, part (232) of the carbon dioxide measurement chamber (202) includes the barbed connectors (250) for the conduit as well as a generally vertical support (233) comprising two posts onto which the carbon dioxide sensor (213) is mounted to ensure adequate gas or air flow around the carbon dioxide sensor (213).

The housing (201) further encloses a light source (215) arranged to irradiate a portion of the conduit (203) and a light sensor (217) that is configured to measure light transmitted through or reflected by the irradiated portion of the conduit (203) to monitor for the potential accumulation of attached material on the conduit (203) and free-floating material near the conduit. The light transmission or reflectance measurements are taken in an optical chamber (235) attached to an end of the central shaft (221) via a screw thread (241).

The optical chamber (235) includes a holder (239) for the LED light source (215) and the conduit (203). The bottom wall (266) of the generally cylindrical holder (239) includes an aperture for the LED light source that is arranged to receive and support the light source within the optical chamber (235). The conduit (203) extends into the holder (239) and its generally straight portion is arranged to be transverse to the generally vertically arranged light source (215) and light sensor (217) of this embodiment. The straight portion (237) of the conduit is supported to lie crosswise to the light source and light sensor by support members (270) provided on the inner surface of the bottom wall (266) of the holder (239). The holder (239) also includes a plurality of openings (268) in its side wall (280) for the ingress of fluid into the holder (239). In this manner, the holder (239) is generally open to allow fluid to be in contact with the straight portion (237) of the conduit (203) so that the outer wall of the conduit (203) provides a fouling surface for any fouling material in the fluid to adhere to and accumulate on.

The optical chamber (235) further includes a light filter holder (251), a spacer member (254) with a light slot (256) and a mounting plate (229) for the light sensor (217). Nitrile O-rings (260) between the light filter holder (251) and the spacer member (254), and between the spacer member (254) and the mounting plate (229), respectively, protect the compartment of the optical chamber (235) housing the light sensor (217) from the ingress of fluid. The light filter holder (251) is secured to an end of the cylindrical holder (239) with screw fasteners (262) and has a central aperture for a light filter (258). The light filter (258) is configured to filter light irradiated by the light source (215) and transmit light of a selected wavelength to the light sensor (217). The light sensor (217) is mounted on the sensor mounting plate (229), which is secured to the central shaft (221) via a screw thread (241) defined therein and to the spacer member (254) with screw fasteners (264). The light filter holder also includes apertures (272) for the conduit (203) to extend through and into the space enclosed by the holder (239). The straight portion (237) of the conduit (203) extends transversely across the space defined between the cylindrical holder (239) and the light filter holder (251) so that the LED light source and the light sensor are on opposite sides of the straight portion (237) of the conduit (203) for light transmission measurements. Light transmission is measured at a predetermined light wavelength as determined by the light filter (258) supported between the conduit (203) and the light sensor (217).

As with the first embodiment, the apparatus (200) shown in FIGS. 6 and 7 is configured to measure at least two fouling parameters in a fluid simultaneously. However, in this second embodiment, the housing is open to the fluid so that the conduit that is within the housing is immersed in fluid whilst a carrier gas, preferably air, is passed through the conduit (203). Accordingly, with the second embodiment microbial metabolism is measured from the surrounding environment, i.e., the fluid surrounding the apparatus when immersed therein. The apparatus housing (201) also encloses the carbon dioxide sensor (213) and light sensor (217), albeit in a different configuration to that of the first embodiment. The second embodiment of the apparatus (200) is similarly capable of real-time monitoring of microbial metabolism in terms of changes in levels of carbon dioxide respired by the microbes that diffuses into the conduit and changes in the amount of fouling material adhering to the wall of the conduit. With the first embodiment the fouling occurs on the internal or inner surface of the conduit as the fluid flows through the conduit and the carrier or sweeper gas flows around the conduit in use. In the second embodiment the fouling occurs on an external or outer surface of the conduit which is in contact with the fluid surrounding it, with the carrier or sweeper gas flowing through the conduit. Accordingly, both embodiments can measure at least two fouling parameters in a fluid simultaneously, but they are configured differently so that the location of the fluid and the carrier gas within the respective apparatuses are inverted relative to one another.

Generally, the second embodiment of the apparatus may find particular use in monitoring fouling parameters in a water treatment system, particularly in a wastewater treatment system, and in cooling waters.

In both exemplary embodiments, the carbon dioxide sensor (113, 213) may be a nondispersive infrared sensor (NDIR) configured to measure carbon dioxide concentrations. It typically has a dynamic range and in effect measures the flux of carbon dioxide across the carbon dioxide permeable membrane. The NDIR sensor may also be configured to measure the temperature and humidity together with the changing carbon dioxide levels in the carbon dioxide measurement chamber.

Many parts of the apparatus, and in particular the housing (101, 201), central shaft (121, 221), guides (123, 223) for the conduit, and the various parts of the optical chamber (135, 235) and carbon dioxide measurement chamber (202) may be made from a plastics material. The housing (101, 201) may be relatively small with a volume ranging between 1 and 2 litres.

The apparatus may be constructed to be modular, small and cost-effective so that it can readily be exchanged for a new one should it malfunction, or the conduit be obstructed or otherwise damaged as a result of fouling.

Figure 8:
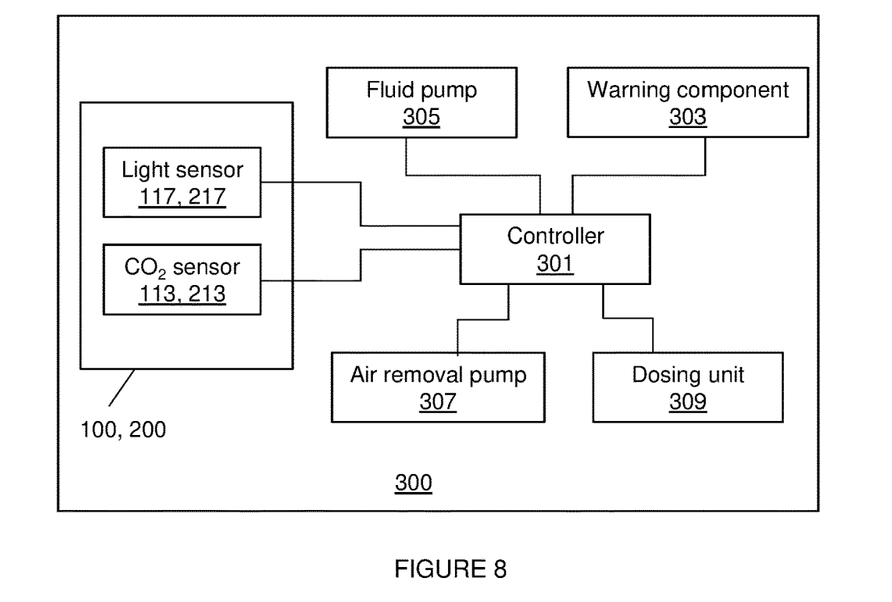
FIG. 8 is a schematic illustration of a system for measuring fouling parameters in a fluid.

The apparatus (100, 200) may form part of a system (300) for monitoring fouling parameters in a fluid shown in FIG. 8. The system comprises a controller (301) which is configured to be in communication with at least the light sensor (117, 217) and the carbon dioxide sensor (113, 213) of the apparatus (100, 200) to continuously monitor the fouling parameters, i.e., the carbon dioxide levels in the housing and the optical light transmission or reflectance data obtained on an irradiated portion of the conduit. If one or more of the fouling parameters reach a preselected threshold level by being at or above the threshold level, the controller (301) may be configured to issue instructions to a warning component (303) to emit a warning signal based on the extent of fouling measured. The controller (301) may also be configured to be in communication with a pump (305) that circulates the fluid through the conduit between the fluid inlet port and the fluid outlet port and the pump (307) that removes air from the housing of the apparatus to control the respective flow rates of both the fluid and the air. As a result of these features, the system (300) can be used as a real-time monitoring system that detects fouling in situ and under continuous flow. The system (300) can also be used to monitor changes in biofilm biomass accumulation and microbial metabolism in response to environmental conditions.

The controller (301) may be further configured to issue instructions to a dosing unit (309) configured to dispense an appropriate amount of an antifouling agent into the fluid.

The antifouling agent may for example be a biocide, a dispersant or a descaling agent, depending on the type or extent of fouling detected.

Advantageously, the apparatus and system described herein is capable of monitoring more than one fouling parameter continuously. The apparatus includes an on-line carbon dioxide sensor for detecting and measuring carbon dioxide respiration. The accumulation of microbial cells within a fluid should result in an increased production and subsequent increased flux of carbon dioxide across the carbon-dioxide permeable membrane provided by the conduit. The apparatus also includes an on-line spectrophotometric measurement system that allows for the non-destructive, high resolution, and real-time monitoring of changes in biofilm biomass and/or the build-up of inorganic matter. Fluctuations of at least these fouling parameters over time can be monitored continuously and analysed to establish a level of fouling, particularly biofouling, in a valuable fluid source, system or process.

The system can provide an early warning of the extent of fouling in a fluid before blockages that causes downtime occurs. The system may also include means of treating the fluid or medium before any potential blockages occurs.

The apparatus may include additional probes that, for example, measure the temperature and pH of the fluid. The controller may continuously monitor the temperature and pH conditions and warn users of any unwanted fluctuations. The pH and temperature information obtained from the probes may also be processed and analysed in order to determine which conditions result in changes in fouling parameters.

The apparatus and system can further be used to evaluate disinfection procedures and develop strategies to manage microbial biofilms. The apparatus and system can for example track the effect of a disinfectant on established microbial communities in cooling water or the like, by measuring the effect of disinfectant dosage on microbial biomass and microbial metabolic rate. Similarly, the effect of temperature changes on biofilms in food processing facilities can for example be analysed by monitoring changes in biofilm biomass spectrophotometrically and the metabolic activity of the biofilms with the carbon dioxide sensor. The apparatus and system may find use in maintaining water quality standards within various industries, including water purification or treatment facilities and food production or processing plants. The system may provide an early warning of deviations from optimal operational parameters by monitoring fouling both in terms of physical fouling as well as metabolic activity. The apparatus and system is scalable and the system modular providing the option of remote monitoring and support.

EXAMPLES

The first embodiment of the apparatus (100) described herein was used to measure the fouling parameters in a fluid, and in particular the effects of changes in nutrient availability and exposure of a biofilm that formed in the conduit to a biocide. A Sensirion SCD30 carbon dioxide sensor and an AMS AS7341 light sensor were used. The light absorbance measurements were done at a wavelength of 595 nm.

The conduit (103) consisting of coiled silicone tubing (2.0 mm inside diameter (I.D.) and 3.0 mm outside diameter (O.D.)) was filled with sterile 3 g/L Trypticasein Soy Broth (TSB) using a peristaltic pump. The system was inoculated by ceasing nutrient flow to the system, followed by injecting 2.0 mL of Pseudomonas sp. strain CT07 (P. fluorescence CT07) standardized to OD595 nm=0.1. The flow was restored after 30 min post-inoculation at a flow rate of 12 mL/h at 22° C. The sweeper gas (air) was pumped into the housing (101) containing the carbon dioxide sensor (113) at a flow rate of 20 ml per minute.

Figure 9:
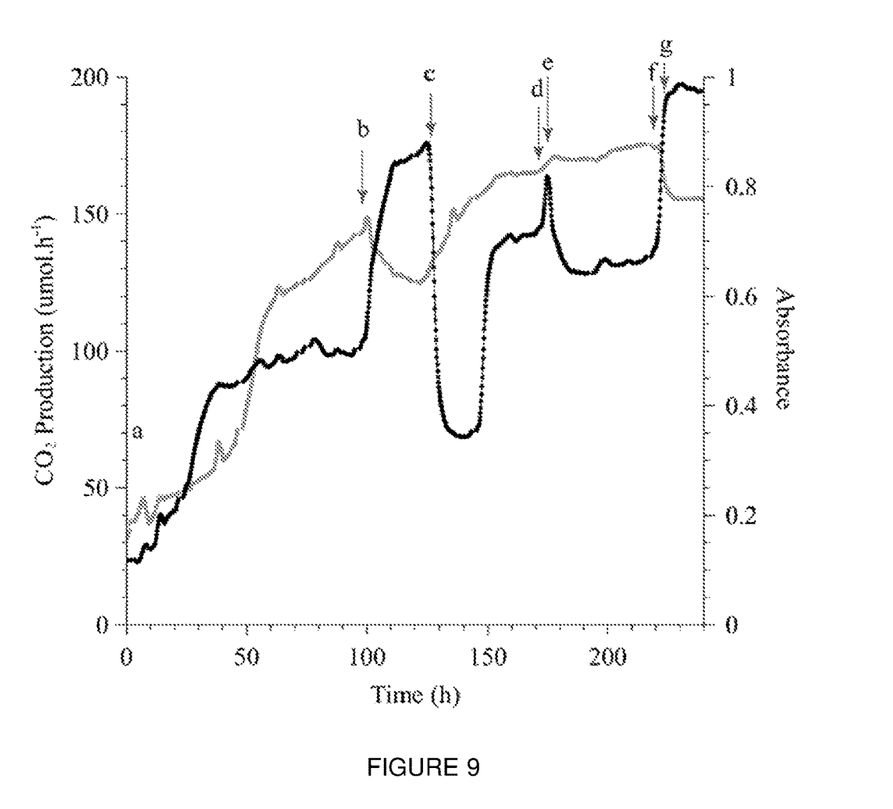
FIG. 9 is a graph of the carbon dioxide production rates (black line) and the light absorbance (grey line) of a *Pseudomonas* sp. CT07 biofilm cultivated under flow and exposed to varying nutrient conditions and a biocide.

The carbon dioxide production rates by microorganisms in the fluid medium was measured with the apparatus (100) as an indicator of the metabolic activity of the microorganisms forming part of the cultivated biofilm. At the same time, the absorbance of the conduit was measured with the apparatus to monitor the amount of biomass on or near the inner surface of the conduit (changes in biofilm thickness and the amount of free-flowing or detached biomass within the medium). The results of the measurements are shown in FIG. 9.

A *P. fluorescence* CT07 biofilm was cultivated under flow of a medium with a nutrient concentration of 3 g/L TSB until a steady state in metabolic activity and biomass was reached (0 to about 90 hours). The carbon dioxide production rates representing the metabolic activity are represented by the black line in FIG. 9 and the absorbance of the irradiated portion of the conduit, representing changes in accumulated biomass, is plotted as a grey line in FIG. 9. The biofilm was exposed to an increased nutrient load of 15 g/L TSB from about 90 to 120 hours which resulted in a marked increase in metabolic activity indicated by the arrow labelled (b) on FIG. 9. At this time the biofilm biomass decreased, presumably due to an increase in osmotic pressure, biofilm sloughing or an increase in planktonic cell yield, or any combination thereof. The nutrient conditions of the biofilm were then reduced to 1.5 g/L TSB from about 120 to 170 hours resulting in a clear decrease in the carbon dioxide production rates, whereas the absorbance increased as shown at the arrow labelled (c) on FIG. 1, demonstrating the utility of the system as a tool to monitor treatment strategies, including optimizations of biocide or bio-dispersant dosing rates. At arrow (d) on FIG. 9, the biofilm was exposed to a low concentration of oxidizing biocide (0.1% Peracetic acid for about 15 min of exposure) which reduced the carbon dioxide production rates and slowed further biomass accumulation. At arrow (e), the biocide was removed and nutrients reintroduced (1.5 g/L TSB from about 165 to 215 hours). Arrow (f) indicates the time at which an increased concentration of the same oxidizing biocide (0.2% Peracetic acid for about 15 min of exposure) was introduced, followed by the introduction of nutrients only (1.5 g/L TSB) at arrow (g) on FIG. 9.

Figure 10:
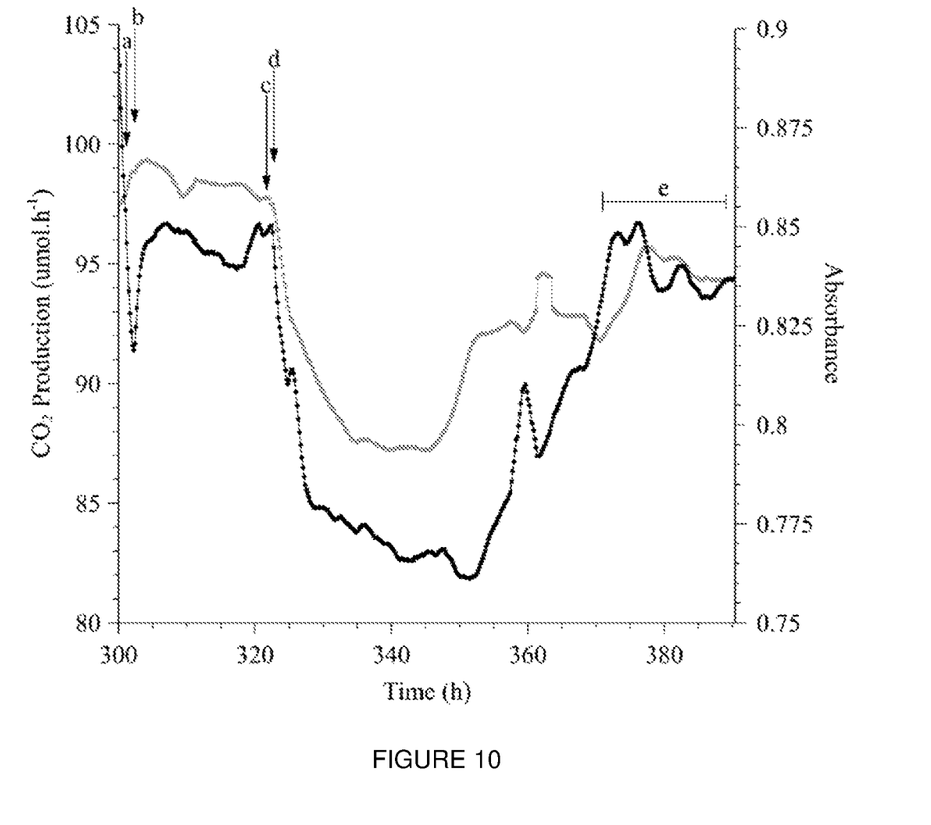
FIG. 10 is a graph of the carbon dioxide production rates and the light absorbance of a *Pseudomonas* sp. CTO7 biofilm cultivated under flow and exposed to varying nutrient conditions and a bio-dispersant.

The effects of introducing various concentrations of a bio-dispersant on fouling parameters of a biofilm were studied. The results in terms of carbon dioxide production rates are plotted as a black line (metabolic activity) and absorbance changes are plotted as a grey line (biomass) in FIG. 10. *P. fluorescence* CT07 was cultivated under continuous flow with a nutrient concentration of 1.5 g/L TSB until a steady state in metabolic activity and biomass was reached (pre-300 hours). From about 300 hours indicated by arrow (a) in FIG. 10, the medium was dosed with a non-ionic surfactant blend (9 mg/L polyethylene-polypropylene glycol bio-dispersant for about 20 minutes) resulting in a substantial reduction in metabolic activity (black line) and accumulation of biomass (grey line). Arrow (b) in FIG. 3 indicates the time at which the bio-dispersant was removed by the reintroduction of nutrients (1.5 g/L TSB from about 301 to 325 hours). At arrow (c) in FIG. 10, an increased concentration of the same bio-dispersant (30 mg/L for about 20 minutes of exposure) was introduced into the culture medium, followed by the introduction of nutrients only (1.5 g/L TSB) at arrow (d). Line (e) on FIG. 10 demonstrates the time at which recovery and establishment of a new steady-state of biofilm metabolic activity and biomass occurs post-exposure to the increased concentration of bio-dispersant (375 h to 390 hours).

The foregoing description has been presented for the purpose of illustration; it is not intended to be exhaustive or to limit the invention to the precise forms disclosed. Persons skilled in the relevant art can appreciate that many modifications and variations are possible in light of the above disclosure. For example, the conduit may be a tube that is at least partially wound or looped within the housing to increase the surface area available for carbon dioxide permeation into the housing, and it need not necessarily be a helical arrangement. It will also be apparent to those skilled in the art, that different optical measurements can be made, by for example irradiating the conduit with light of one or more selected wavelengths and using light sensors or detectors which may be optimised for single wavelength detection, to determine the presence of different fouling parameters, whether it be the presence of living or non-living and organic or inorganic materials. The optical measurements may also be conducted in any direction relative to the straight portion of the conduit, as long as a surface of the conduit exposed to fluid or liquid medium is appropriately irradiated and absorbance or reflectance measurements can be made with the light sensor.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Finally, throughout the specification and accompanying claims, unless the context requires otherwise, the word 'comprise' or variations such as 'comprises' or 'comprising' will be understood to imply the inclusion of a stated integer or group of integers but not the exclusion of any other integer or group of integers.

The invention claimed is:

1. An apparatus for measuring fouling parameters in a fluid comprising:
- a housing;
- a conduit within the housing, wherein at least a portion of the conduit provides a carbon dioxide permeable membrane;
- a carbon dioxide sensor within the housing configured to measure carbon dioxide levels at the sensor;
- a light source within the housing that irradiates a portion of the conduit;
- a light sensor within the housing configured to measure light transmitted through or reflected by the irradiated portion of the conduit; and
- wherein a controller is configured to receive a signal from the light sensor and process the signal to monitor the extent of biofouling or scaling of the conduit and to receive a signal from the carbon dioxide sensor and process the signal to monitor the levels of carbon dioxide produced by microbes in the fluid.

2. The apparatus as claimed in claim 1, wherein the conduit is a tube that is at least partially wound or looped within the housing.

3. The apparatus as claimed in claim 2, wherein the housing is generally cylindrical and the tube is partially wound into a coil.

4. The apparatus as claimed in claim 3, wherein the tube is coiled around a central shaft mounted centrally within the cylindrical housing.

5. The apparatus—as claimed in claim 4, wherein the central shaft includes a plurality of guides for the coiled tube that are arranged to space helical rings of the coiled tube apart.

6. The apparatus as claimed in claim 1, wherein the conduit is formed from a carbon dioxide permeable silicone membrane.

7. The apparatus as claimed in claim 1, wherein the conduit carries the fluid through the housing and has one end at a fluid inlet port of the housing and an opposite end at a fluid outlet port of the housing.

8. The apparatus as claimed in claim 7, wherein changes in the carbon dioxide levels as measured by the carbon dioxide sensor indicate a relative amount of carbon dioxide diffusing through the carbon dioxide permeable membrane.

9. The apparatus as claimed in claim 7, further including a pump configured to circulate the fluid between the fluid inlet port and the fluid outlet port.

10. The apparatus as claimed in claim 7, wherein the housing includes an air inlet port and an air outlet port, the air outlet port including an elongate pipe that extends into the housing, the elongate pipe having an open end near the carbon dioxide sensor and the air outlet port being connected to a pump for continuous removal of air from the housing.

11. The apparatus as claimed in claim 1, wherein the housing includes a plurality of openings for the fluid so that, in use, the conduit is immersed in the fluid with the conduit carrying a carrier gas and having one end at an gas inlet port of the housing and an opposite end at a gas port into a carbon dioxide measurement chamber which includes the carbon dioxide sensor, the carbon dioxide sensor being configured to measure the carbon dioxide levels in the carbon dioxide measurement chamber.

12. The apparatus—as claimed in claim 11, further including a pump configured to continuously circulate carrier gas between the gas inlet port and a gas vent provided in the carbon dioxide chamber through which the carrier gas may exit in use.

13. The apparatus as claimed in claim 11, wherein the carbon dioxide sensor is mounted on a generally vertical support to, in use, ensure adequate gas flow around the carbon dioxide sensor.

14. The apparatus as claimed in claim 1, wherein the conduit includes a generally straight portion that extends through an optical chamber which houses the light source and the light sensor on opposite sides of the generally straight portion of the conduit.

15. The apparatus as claimed in claim 14, wherein the light source is a light emitting diode and the light sensor is a digital light sensor that measures light transmission through the conduit.

16. The apparatus as claimed in claim 14, wherein the optical chamber also includes a light filter arranged to filter the light from the light source to light of a selected wavelength before measurement thereof by the light sensor.

17. A system for monitoring fouling parameters in a fluid comprising the apparatus as claimed in claim 1, wherein the controller is an external processing module configured to be in communication with a processing module of the apparatus to continuously monitor measured fouling parameters.

18. The system as claimed in claim 17, wherein the controller emits a warning signal if the fouling parameters measured by the apparatus and monitored by the controller reach a selected threshold level.

19. The system as claimed in claim 17, wherein the controller is further configured to issue instructions to dispense an antifouling agent into the fluid.

* * * * *